US012678380B2

(12) United States Patent
Jung et al.

(10) Patent No.: US 12,678,380 B2
(45) Date of Patent: Jul. 14, 2026

(54) SKIN-ATTACHABLE PATCH AND METHOD FOR USING SKIN-ATTACHABLE PATCH

(71) Applicant: BIOSENSOR LABORATORIES INC., Seoul (KR)

(72) Inventors: Min Woong Jung, Seoul (KR); Myoung Hoon Jang, Seoul (KR)

(73) Assignee: Biosensor Laboratories Inc., Seoul (KR)

( * ) Notice: Subject to any disclaimer, the term of this patent is extended or adjusted under 35 U.S.C. 154(b) by 247 days.

(21) Appl. No.: 18/514,871

(22) Filed: Nov. 20, 2023

(65) Prior Publication Data

US 2024/0082607 A1     Mar. 14, 2024

Related U.S. Application Data

(63) Continuation of application No. PCT/KR2022/016541, filed on Oct. 27, 2022.

(30) Foreign Application Priority Data

| | | |
|---|---|---|
| Nov. 1, 2021 | (KR) ........................ | 10-2021-0148169 |
| Feb. 24, 2022 | (KR) ........................ | 10-2022-0024662 |

(51) Int. Cl.
| | |
|---|---|
| *A61Q 17/00* | (2006.01) |
| *A61G 19/00* | (2006.01) |
| *A61K 8/02* | (2006.01) |
| *A61Q 19/00* | (2006.01) |

(52) U.S. Cl.
CPC ............ *A61K 8/0208* (2013.01); *A61G 19/00* (2013.01); *A61Q 17/00* (2013.01)

(58) Field of Classification Search
None
See application file for complete search history.

(56) References Cited

U.S. PATENT DOCUMENTS

| | | | |
|---|---|---|---|
| 10,751,266 | B2 | 8/2020 | Boswell et al. |
| 10,806,681 | B2 | 10/2020 | Boswell et al. |
| 2002/0110585 | A1 | 8/2002 | Godbey et al. |
| 2021/0137628 | A1 | 5/2021 | Robinson et al. |
| 2021/0137799 | A1 | 5/2021 | Watanabe et al. |

FOREIGN PATENT DOCUMENTS

| | | |
|---|---|---|
| CN | 1452478 A | 10/2003 |
| CN | 208573866 U | 3/2019 |
| CN | 11002616 A | 7/2019 |
| CN | 111698984 A | 9/2020 |
| CN | 112384195 A | 2/2021 |

(Continued)

OTHER PUBLICATIONS

English language translation of KR 10-2011-0062277 A, Publ. Jun. 10, 2011. (Year: 2011).*

(Continued)

*Primary Examiner* — Dominic Lazaro
(74) *Attorney, Agent, or Firm* — Knobbe, Martens, Olson & Bear, LLP

(57) ABSTRACT

Proposed are a patch for attachment on the skin and a method of using the patch for attachment on the skin. The patch includes a base sheet and a film which is disposed on the base sheet and of which thickness is decreased by an activating material.

6 Claims, 14 Drawing Sheets

(56)                    References Cited

FOREIGN PATENT DOCUMENTS

| JP | 2000-128781 | A |   | 5/2000 |   |
|----|-------------|---|---|--------|---|
| JP | 2003-515556 | A |   | 5/2003 |   |
| JP | 2003-530421 | A |   | 10/2003 |   |
| JP | 2004-231516 | A |   | 8/2004 |   |
| JP | 2009-091371 | A |   | 4/2009 |   |
| JP | 2013-184970 | A |   | 9/2013 |   |
| JP | 2014-065681 | A |   | 4/2014 |   |
| JP | 2014-233956 | A |   | 12/2014 |   |
| JP | 2020-074847 | A |   | 5/2020 |   |
| JP | 2020-515509 | A |   | 5/2020 |   |
| KR | 10-2006-0133139 | A |   | 12/2006 |   |
| KR | 10-2008-0014461 | A |   | 2/2008 |   |
| KR | 10-2011-0062277 | A |   | 6/2011 |   |
| KR | 20110062277 | A | * | 6/2011 | .......... A61K 8/9789 |
| KR | 10-2013-0012034 | A |   | 1/2013 |   |
| KR | 20-2017-001781 | U |   | 5/2017 |   |
| KR | 10-795709 | B1 |   | 12/2017 |   |
| KR | 10-2018-0067177 | A |   | 6/2018 |   |
| KR | 10-2020-0045125 | A |   | 5/2020 |   |
| KR | 10-2021-0027208 | A |   | 3/2021 |   |
| KR | 10-2021-0038434 | A |   | 4/2021 |   |
| TW | M533991 | U |   | 12/2016 |   |
| WO | WO 2004/077988 | A1 |   | 9/2004 |   |
| WO | WO 2021/040498 | A1 |   | 3/2021 |   |
| WO | WO 2021/161215 | A1 |   | 8/2021 |   |
| WO | WO 01/78678 | A1 |   | 10/2021 |   |

OTHER PUBLICATIONS

Bathe, R. & Kapoor, R., Transdermal drug delivery system: formulation, development and evaluation—An overview, Int. J. Biomed Adv. Res., 6 (2015) pp. 1-10. (Year: 2015).*
Peng, Y. et al., Melting of Colloidal Crystal Films, Phys. Rev. Lett., 104 (2010) 205703, pp. 1-4. (Year: 2010).*
International Search Report and Written Opinion mailed Feb. 8, 2023 in International Application No. PCT/KR2022/016541, *English translation of ISR.*
International Search Report and Written Opinion mailed Feb. 8, 2023 in International Application No. PCT/KR2022/016545, *English translation of ISR.*
Office Action received in JP Application No. 2023-573126 dated Oct. 1, 2024.
Extended European Search Report received in EP Application No. 22887632.2 dated Jan. 24, 2025.
Office Action received in JP Application No. 2023-573115 dated Feb. 4, 2025.
Extended European Search Report received in EP Application No. 22887634.8 dated Feb. 4, 2025.
Office Action dated Dec. 27, 2025 in Chinese Application No. 202280037356.5, in 9 pages.

* cited by examiner (A)                    (B)

SKIN-ATTACHABLE PATCH AND METHOD FOR USING SKIN-ATTACHABLE PATCH

CROSS-REFERENCE TO RELATED APPLICATION

This application is a continuation of International Application No. PCT/KR2022/016541, filed on Oct. 27, 2022, which claims the benefit of Korean Patent Application No. 10-2021-0148169, filed on Nov. 1, 2021, and Korean Patent Application No. 10-2022-0024662, filed on Feb. 24, 2022 in the Korean Intellectual Property Office, the entire disclosure of each of which is incorporated herein by reference.

This application relates to and is concurrently filed with U.S. Patent Application entitled "SKIN-ATTACHMENT PATCH AND METHOD FOR MANUFACTURING SKIN-ATTACHMENT PATCH" which is incorporated herein by reference.

BACKGROUND

Technical Field

The present disclosure relates to a patch for attachment on skin and a method of using the patch.

Description of Related Technology

In general, a skin patch is used for skin beauty such as ultraviolet (UV) blocking or moisturizing, and a general nonwoven fabric impregnated with various preparations such as essence is attached on the skin or a hydrogel state may be attached on the skin.

SUMMARY

One aspect is a skin attachment patch having high skin adhesion and transparency, and a method of using the same.

Another aspect is a patch for attachment on the skin, the patch including a base sheet and a film which is disposed on the base and of which thickness is decreased by an activating material.

In an embodiment, when the film is activated by the activating material, the transparency thereof may be increased.

In an embodiment, the active material may be sprayed on the film, applied on the film, or secreted from the skin on which the film is attached.

In an embodiment, when the film is activated, softness thereof may be increased.

In an embodiment, the activating material may melt the film.

In an embodiment, the film may include a first layer adjacent to the base sheet, and a second layer which is disposed on one side of the first layer and includes an effective material to be delivered to the skin.

In an embodiment, an interlayer may be disposed between the first layer and the base sheet, and may have a lower adhesive force than that of the second layer.

In an embodiment, the adhesive force of the interlayer may be decreased when the interlayer is in contact with a solution.

Another aspect is a method of using the skin attachment patch, wherein the skin attachment patch has a base sheet and a film. The method includes: attaching the film on the skin; and decreasing the thickness of the film by an activating material.

In an embodiment, the attaching the film may include decreasing the adhesive force between the base sheet and the film by allowing the base sheet to absorb a solution, attaching the base sheet and the film on the skin, and separating the base sheet from the film.

In an embodiment, the decreasing of the thickness of the film may include decreasing the thickness of the film when the activating material comes into contact with the film.

In an embodiment, in the decreasing of the thickness of the film, the activating material may be secreted from the skin on which the film is attached.

In an embodiment, in the decreasing of the thickness of the film, the activating material may melt the film.

BRIEF DESCRIPTION OF THE DRAWINGS

The above and other aspects, features, and advantages of certain embodiments of the disclosure will be more apparent from the following description taken in conjunction with the accompanying drawings.

Figure 1:
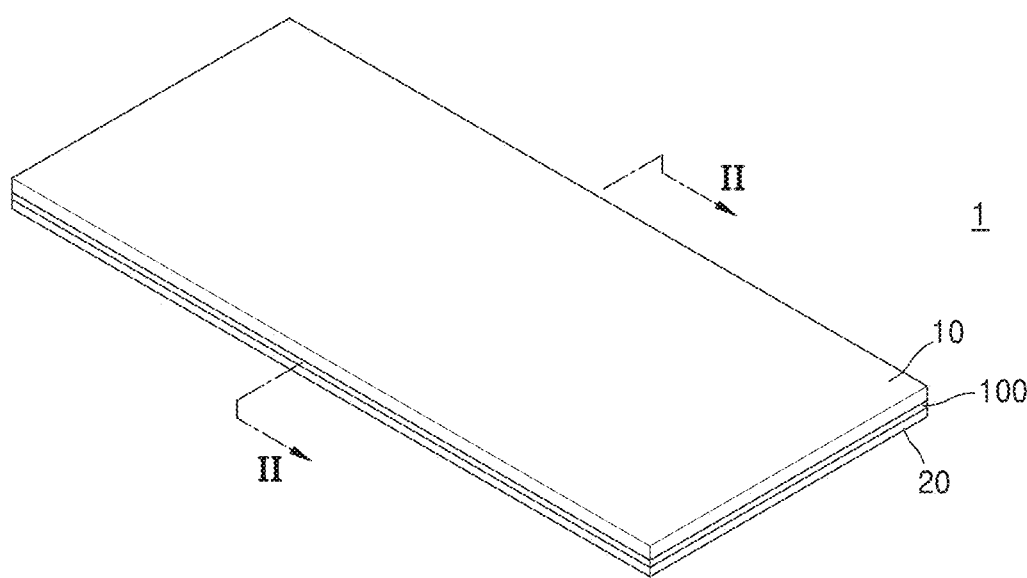
FIG. 1 is a view showing a skin attachment patch according to an embodiment of the present disclosure.
Figure 14:
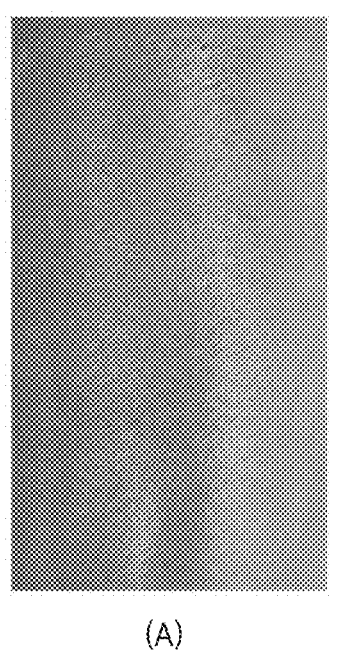
Figure 14:
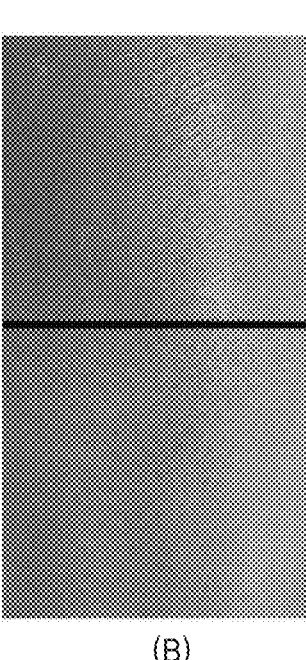

(A) and (B) of FIG. 14 show images of the patch for attachment on the skin of FIG. 1 during use on the skin.

DETAILED DESCRIPTION

As other skin patches, a gel-type patch using agar or starch is used. As described above, when the general nonwoven fabric impregnated with various preparations such as essence is attached on the skin, such as the face, the amount thereof evaporated into the air is high and thus, the essence is completely dried up in about 15 to 20 minutes, and the stickiness thereof is deteriorated, resulting in, for example, separation from the skin or deterioration of transdermal absorption of the preparation.

In addition, in the case of the hydrogel-type patch, adhesion to the skin is poor, sticky preparations providing adhesion cause chemical skin troubles, the production is limited due to limited preparations, the manufacturing process is complicated, and, for example, aging requires a long time, leading to high manufacturing costs.

In addition, in the case of a gel-type patch using agar or starch, a mesh or the like is used as a support for the gel. Accordingly, the support does not perfectly support the gel, so that the shape is disturbed or damaged while the user attaches the same on the skin, After drying, the residue turns into powder, which makes it difficult to maintain cleanliness.

Recently, as the leisure industry such as golf, mountaineering and hiking is expanding, patches for use in activities or outdoors, as well as indoors, are required.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The present disclosure may be subjected to various modifications and may have various embodiments. Accordingly, specific embodiments are illustrated in the drawings and described in detail in the detailed description. Effects and features of the present disclosure, and a method of achieving the same will become clear with reference to the embodiments described below in detail in conjunction with the drawings. However, the present disclosure is not limited to the embodiments provided below and may be implemented in various forms.

Hereinafter, embodiments of the present disclosure will be described in detail with reference to the accompanying drawings, and when described with reference to the drawings, the same or corresponding components are given with the same reference numerals, and the overlapping description thereof will be omitted.

In the following embodiments, terms such as first, second, etc. are used for the purpose of distinguishing one component from another, not to limit terms modified thereby.

In the following examples, the singular expression includes the plural expression unless the context clearly dictates otherwise.

In the following embodiments, terms such as "include" or "have" refer to the case in which the features or components described in the specification are present, and the case that one or more other features or components will be added, is not excluded.

In the following embodiments, when it is said that a part such as a film, region, or component is on or above another film, region, or component, this case includes not only a case where a film, region, or component is directly on another film, region, or component, but also a case where other film, region, component, etc. is interposed therebetween.

In the drawings, the size of the components may be exaggerated or decreased for convenience of description. For example, since the size and thickness of each component shown in the drawings are arbitrarily indicated for convenience of description, the present disclosure is not limited to the embodiments illustrated in the drawings.

Figure 2:
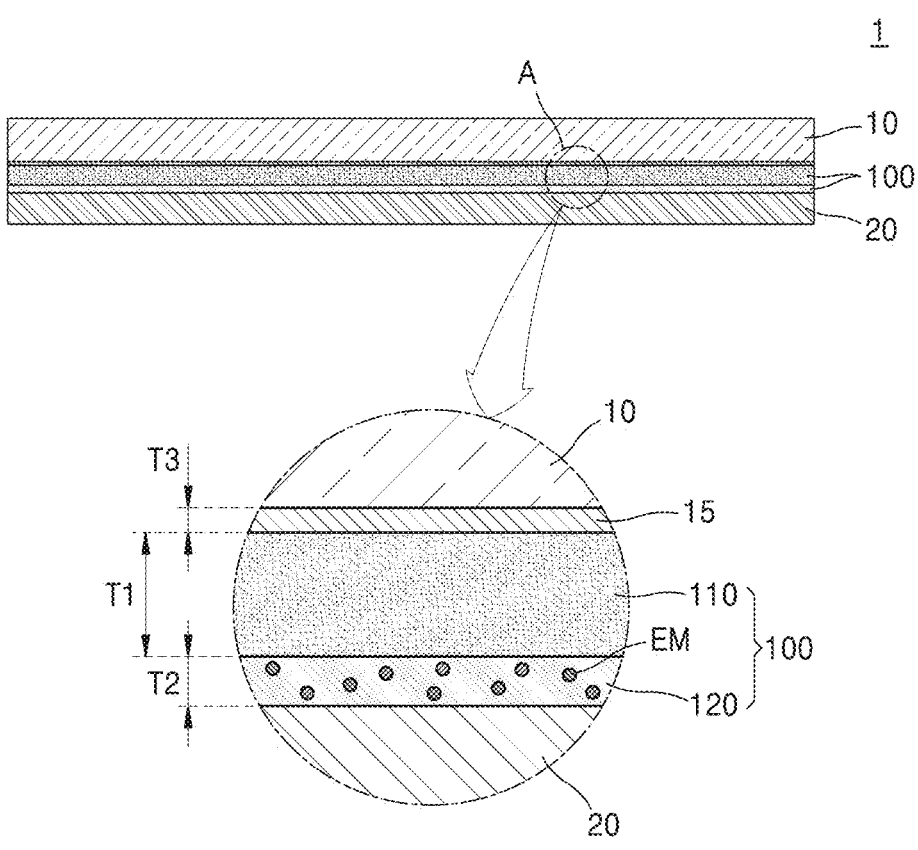
FIG. 2 is a cross-sectional view taken along line II-II of FIG. 1, and an enlarged view thereof.

FIG. 1 is a view showing a skin attachment patch according to an embodiment of the present disclosure, and FIG. 2 is a cross-sectional view taken along line II-II of FIG. 1, and an enlarged view thereof.

Referring to FIGS. 1 and 2, a skin attachment patch 1 includes a film 100. The film 100 is attached on the skin, and depending on the function of the film 100, the film 100 may deliver an effective material to the skin or may protect the skin from the external environment.

The skin attachment patch 1 may have flexibility to increase adhesion to the skin. The skin attachment patch 1 may have elasticity so that the skin attachment patch 1 may be attached to various locations on the body.

The skin attachment patch 1 may have various shapes and sizes depending on the location where it is attached or the purpose of use. For example, the skin attachment patch 1 may have various shapes such as polygons, circles, and ovals. In an embodiment, the skin attachment patch 1 may have various sizes depending on the area the skin attachment patch 1 covers. However, hereinafter, for convenience of explanation, an embodiment in which the skin attachment patch 1 has a rectangular shape as shown in FIG. 1, will be described.

The skin attachment patch 1 may include a base sheet 10 and the film 100.

The base sheet 10 supports the film 100, one side of the base sheet 10 is exposed to the outside, and another side of the base sheet 10 may face the film 100.

In an optional embodiment, an interlayer 15 may be disposed between the base sheet 10 and the film 100. The interlayer 15 may have an adhesive force so that the film 100 is attached on the base sheet 10. The film 100 may be supported on the base sheet 10 via the interlayer 15.

The adhesive force of the interlayer 15 may be changed by an additive material. Once the film 100 is attached on the skin, the adhesive force of the interlayer 15 may be decreased to allow the base sheet 10 to be easily removed from the film 100. For example, the adhesive force of the interlayer 15 may be decreased after being in contact with a solution, and once the adhesive force of the interlayer 15 is decreased, the base sheet 10 may be easily removed from the film 100.

In an embodiment, the interlayer 15 may have decomposition properties, and may be decomposed by a liquid. For example, the interlayer 15 may be dissolved by water, and when the base sheet 10 is sufficiently wetted with water, a portion of interlayer 15 may be decomposed. When the interlayer 15 is decomposed, the adhesive force between the base sheet 10 and the film 100 may be decreased, and thus, the base sheet 10 may be easily separated from the film 100.

In another embodiment, the interlayer 15 may have a lower adhesive force than the second layer 120 of the film 100. When the base sheet 10 is removed after the second layer 120 of the film 100 is attached on the skin, since the adhesive force between the second layer 120 and the skin may be less than the adhesive force between the base sheet 10 and the interlayer 15 or the adhesive force between the first layer 110 and the interlayer 15, the base sheet 10 may be easily removed.

In an optional embodiment, the skin attachment patch 1 may further include a liner sheet 20. The liner sheet 20 may cover one side of the film 100 to protect the surface of the film 100 attached on the skin. The liner sheet 20 may be separated from the film 100 when the film 100 is attached on the skin.

The film 100 may be placed on the base sheet 10. The film 100 may be placed between the base sheet 10 and the liner sheet 20. The film 100 may have flexibility and elasticity so as to be in close contact with the skin on which the same is to be attached, and may be formed of a biocompatible material.

Hereinafter, the activation of the film 100 is defined as a change in the state of the film 100 when an activating material AM is in contact with the film 100 (see FIG. 7). For example, when the film 100 is activated, the thickness of the film 100 may be decreased or the adhesion thereof to the skin may be increased, or the film 100 has higher transparency, so that the skin region on which the film 100 is attached may be viewed from the outside as being transparent. In an embodiment, when the film 100 is activated, the softness of the film 100 may be increased so that the film 100 may be soften.

The activating material AM may be defined as a material that changes the state of the film 100 to the active state. The activating material AM may react with the film 100 to change the state of the film 100.

The activating material AM may be in the form of a liquid or gel that is applied or sprayed to the film 100. For example, the activating material AM may be water applied or sprayed on the surface of film 100, or cosmetics such as toners and creams.

The activating material AM may be a secretion secreted by the skin. When secretions are generated in the area on which film 100 is attached, the film 100 may absorb the secretions and be activated.

Figure 7:
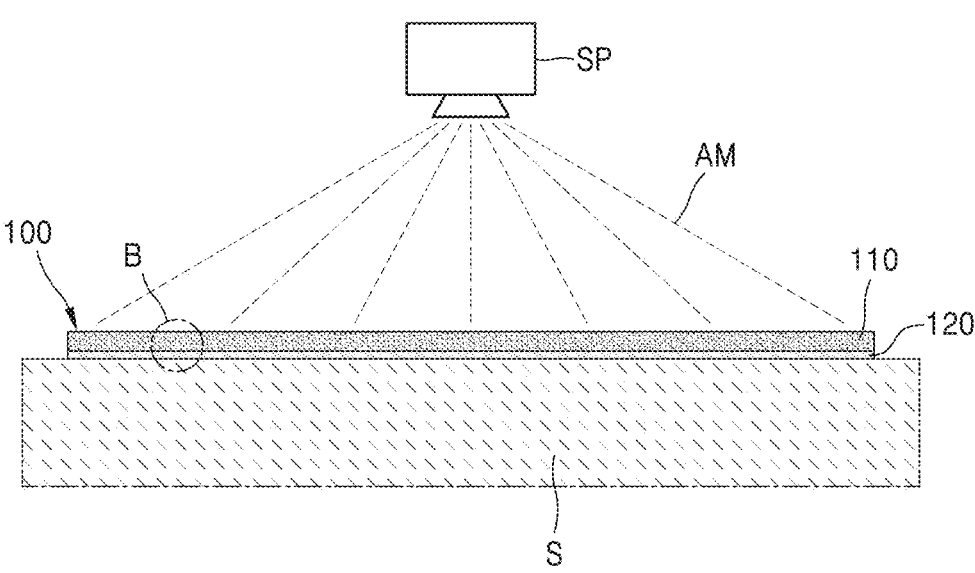

In an embodiment, when the film 100 is attached on the skin as shown in FIG. 7, the activating material AM may be sprayed to the outside of the film 100 by a tool such as a spray SP.

In another embodiment, before the film 100 is attached on the skin, the user may apply the activating material AM on the skin, and then attach the film 100 thereon. Over time, the activating material may melt the film 100, causing the film 100 to become activated.

The film 100 may have a multi-layer structure. For example, the film 100 may include a first layer 110 and a second layer 120.

The first layer 110 may be placed adjacent to the base sheet 10. The first layer 110 may be formed of a biocompatible material and be activated by the activating material AM.

A portion of the first layer 110 may be melted by the activating material AM and thus, the thickness of the first layer 110 may be decreased. When the thickness of the first layer 110 is decreased, the film 100 may adhere more closely to a skin S, resulting in higher transparency. Thus, even when the film 100 is attached on the skin, the skin may be exposed to the outside without any sense of heterogeneity.

The first layer 110 may be formed of a material that is capable of being melted by the activating material AM. The first layer 110 may be formed of a material that decomposes when in contact with the activating material AM.

In an embodiment, the first layer 110 may be formed using polyurethane. The activating material AM may react with polyurethane to reduce the thickness of the first layer 110. The activating material AM may reduce the thickness of the first layer 110 by melting the polywool of polyurethane.

The first layer 110 may additionally include an effective material (not shown) depending on the use of the skin attachment patch 1.

In an embodiment, the first layer 110 may include a UV blocking material. The skin attachment patch 1 may block UV rays in the area where the film 100 is attached.

When the film 100 is activated, the transparency of the film 100 is increased. Accordingly, the skin attachment patch 1 may have a UV blocking effect without cloudiness. In an embodiment, when the film 100 is activated, the film 100 becomes thinner so that the film 100 may be attached in a certain area without a sense of heterogeneity.

In another embodiment, the first layer 110 may have a mark or symbol (not shown) printed therein. When the film 100 attached on the skin is activated, the first layer 110 becomes thinner, and thus, the transparency of the first layer 110 is increased and the mark or symbol may become clearer.

The second layer 120 may be in contact with the skin and may have adhesive properties. The second layer 120 may be supported on the liner sheet 20, and may fix the first layer 110 on the skin S.

In an optional embodiment, the second layer 120 may include an effective material EM. The effective material EM may be defined as a material to be delivered into the body through the skin on which film 100 is attached, and may be, for example, drugs, cosmetics, and functional materials.

Figure 9:
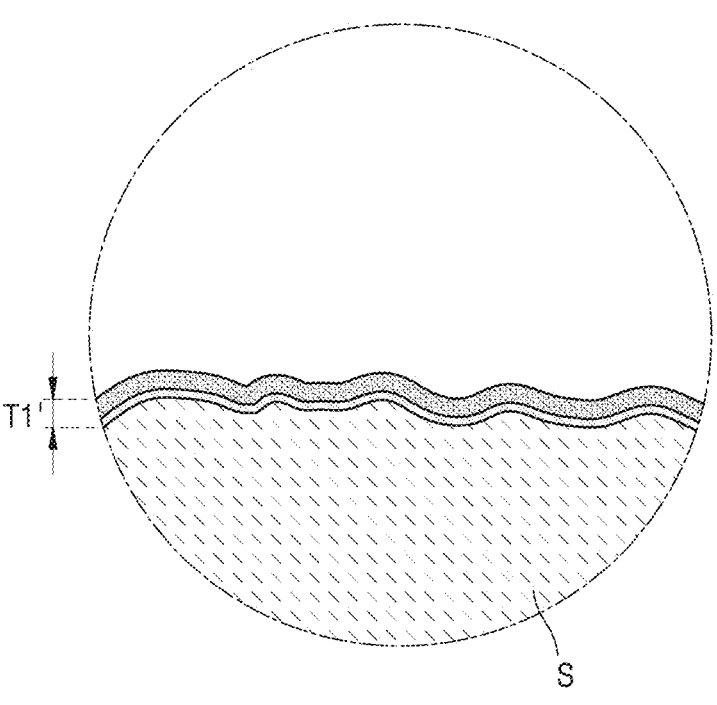

The first layer 110 may have a first thickness T1, and the second layer 120 may have a second thickness T2, which is less than that of the first layer 110. Referring to FIG. 9, when the film 100 is activated, the thickness of the first layer 110 may be decreased from a first thickness T1 to a first' thickness T1'.

The interlayer 15 may have a third thickness T3, the third thickness T3 may be set to be less than the second thickness T2. The interlayer 15 may be placed between the first layer 110 and the base sheet 10, and the adhesive force thereof may be less than that of the second layer 120.

The adhesive force of the interlayer 15 may be changed by an additive material. When the additive material is absorbed by the interlayer 15, the adhesive force of the interlayer 15 may be decreased. For example, when a liquid additive material is absorbed by the interlayer 15, the type of the interlayer 15 is changed to a gel or liquid, so that the base sheet 10 may slide easily on the film 100.

Figure 3:
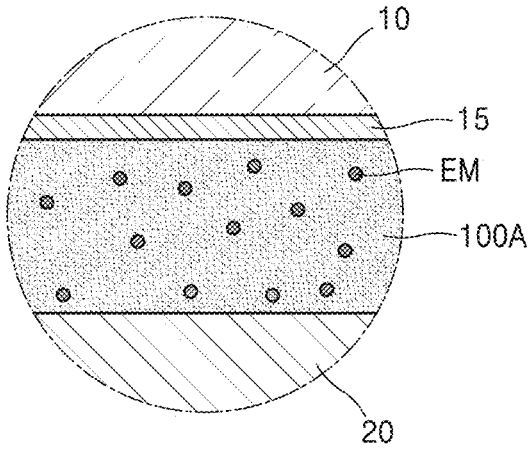
FIG. 3 is an enlarged view of a modified example of the structure illustrated in FIG. 2.

FIG. 3 is an enlarged view of a modified example of the structure illustrated in FIG. 2. FIG. 3 shows an enlarged view of region A of FIG. 2.

Referring to FIG. 3, the patch for attachment on the skin may include a film 100A disposed between the base sheet 10 and the liner sheet 20. The interlayer 15 may be placed between the base sheet 10 and the film 100A.

The film 100A may have a single-layer structure, and a portion thereof which is adjacent to the liner sheet 20 may have an adhesive force to be attached on the skin.

The film 100A may be formed of a material that melts by the activating material AM, and a portion of the film 100A melts so that the film 100A is in more adhesive to the skin and transparency thereof may be increased. For example, the film 100A may be formed of polyurethane as in the first layer 110 described above.

In an optional embodiment, the film 100A may include an effective material EM. In an embodiment, the effective material EM may be, for example, drugs, cosmetics, and functional substances that can be delivered into the body through the skin S.

In an embodiment, the effective material EM may include a material that protects the skin S. In an embodiment, the effective material EM may be a material which is not delivered to the skin S, and which protects the skin from the external environment. An example of the material is a sunscreen.

Figure 10:
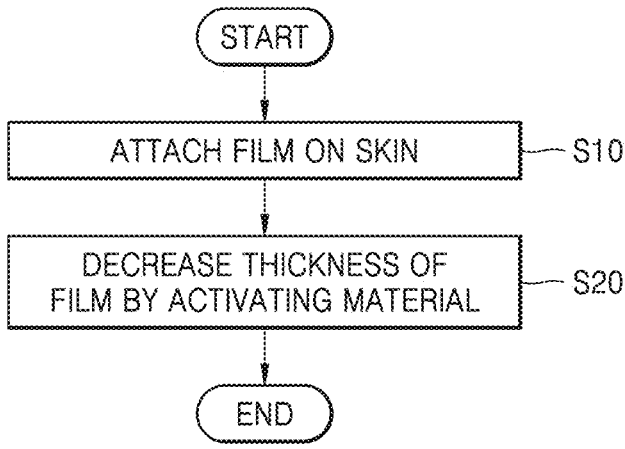
FIGS. 10 and 11 are flowcharts illustrating a method of using the skin attachment patch illustrated in FIG. 1.
Figure 11:
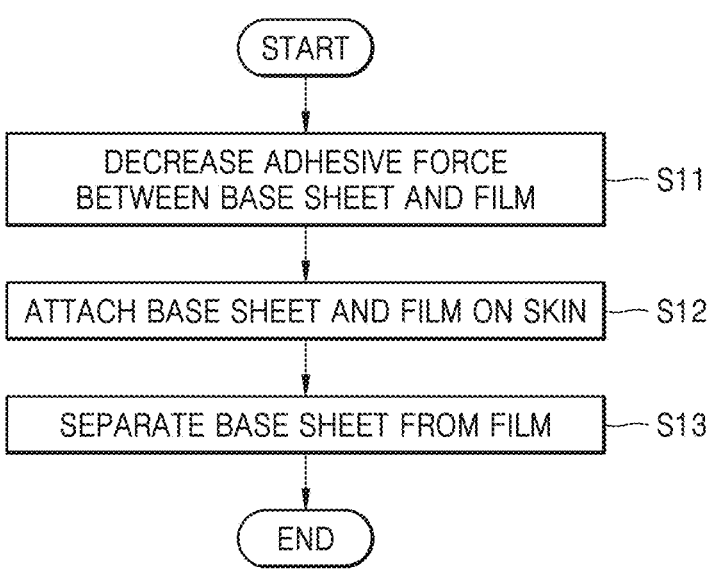

FIGS. 4 to 9 are diagrams illustrating a method of using the skin attachment patch illustrated in FIG. 1, and FIGS. 10 and 11 are flowcharts illustrating a method of using the patch for attachment on the skin illustrated in FIG. 1.

Referring to FIGS. 4 to 11, a method of using the skin attachment patch 1 may include attaching a film on the skin (S10) and decreasing the thickness of the film by an activating material (S20).

The attaching the film (S10) may include decreasing the adhesive force between the base sheet and the film by allowing the base sheet to absorb a solution (S11), attaching the base sheet and the film on the skin (S12), and separating the base sheet from the film (S13).

Figure 4:
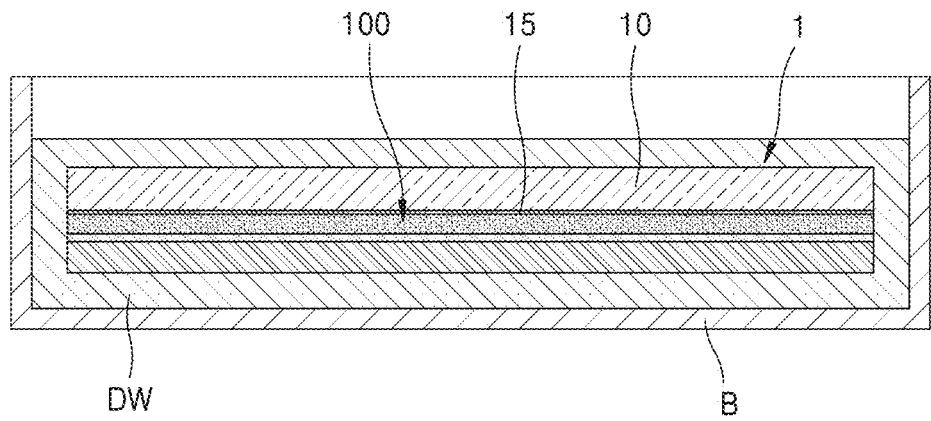
FIGS. 4 to 9 are diagrams illustrating a method of using the skin attachment patch illustrated in FIG. 1.

Referring to FIG. 4, in the decreasing the adhesive force between the base sheet and the film by allowing the base sheet to absorb a solution (S11), the adhesive force of the interlayer 15 of the skin attachment patch 1 may be decreased.

For the skin attachment patch 1, the additive material is absorbed by the interlayer 15, and the adhesive force of the interlayer 15 may be decreased. The additive material, which is a solution, may be absorbed by the interlayer 15 in various ways.

In an embodiment, when the skin attachment patch 1 is immersed in a solution DW stored in a container B as illustrated in FIG. 4, the solution DW is absorbed by the base sheet 10 and penetrates into the interlayer 15. The adhesive force of the interlayer 15 may be decreased by the solution DW.

As another example, by spraying the solution DW from the top or side of the base sheet 10, the solution DW may penetrate into the interlayer 15. The adhesive force of the interlayer 15 may be decreased by the solution DW.

Although the drawing shows that the liner sheet 20 is removed after the solution DW is absorbed by the skin attachment patch 1, embodiments of the present disclosure are not limited thereto. Before the liner sheet 20 is removed from the skin attachment patch 1 and the film 100 is attached to the skin S, the solution DW may be absorbed by the skin attachment patch 1.

Figure 5:
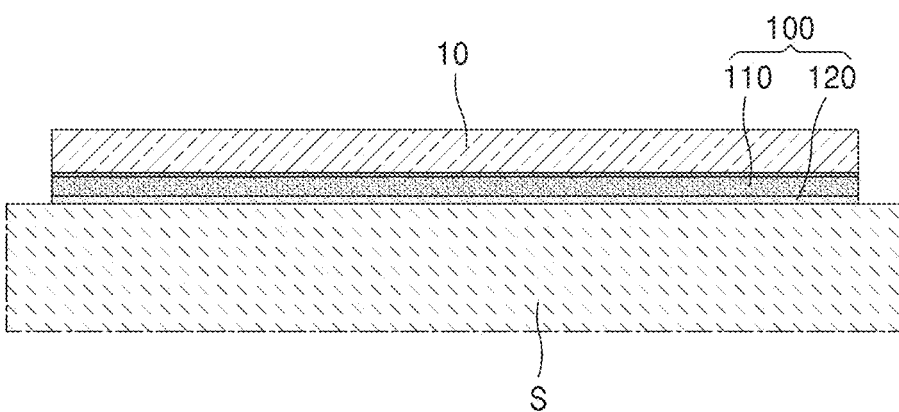

Referring to FIG. 5, in the attaching the base sheet and the film on the skin (S12), the skin attachment patch 1 may be attached to the skin S, after the liner sheet 20 is removed. Due to the adhesive force of the second layer 120, the skin attachment patch 1 may be fixed on the skin S.

Figure 6:
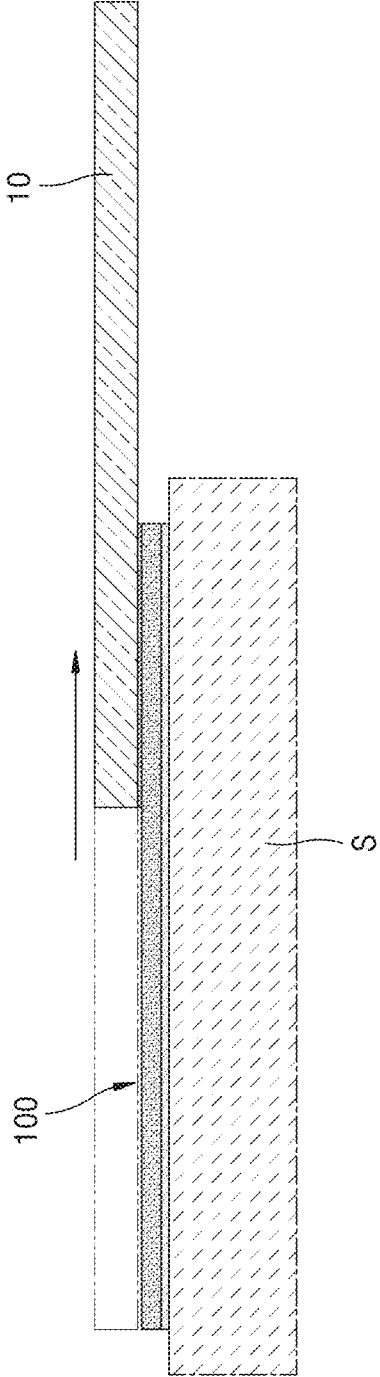

Referring to FIG. 6, in the separating the base sheet from the film (S13), the base sheet 10 may be removed. Since the adhesive force of the interlayer 15 is decreased due to the solution DW, the user may simply separate the base sheet 10 from the film 100.

In another embodiment, the attaching the film (S10) may include attaching the base sheet and the film on the skin (S12) and separating the base sheet from the film (S13). By forming the interlayer 15 having a smaller adhesive force than the second layer 120, the decreasing the adhesive force between the base sheet and the film by allowing the base sheet to absorb the solution (S11) may be omitted.

The interlayer 15 may have a lower adhesive force than the second layer 120 of the film 100. When the base sheet 10 is removed after the second layer 120 of the film 100 is attached on the skin, since the adhesive force between the second layer 120 and the skin may be less than the adhesive force between the base sheet 10 and the interlayer 15 or the adhesive force between the first layer 110 and the interlayer 15, the base sheet 10 may be easily removed.

Referring to FIG. 7, in the decreasing of the thickness of the film by the activating material (S20), the activating material AM may be applied or sprayed onto the film 100.

In an embodiment, the activating material AM may be sprayed to the first layer 110 of the film 100 by the spray SP as illustrated in FIG. 7. When the activating material AM reacts with the first layer 110, the thickness of the first layer 110 may be decreased and the softness thereof may be increased.

In an optional embodiment, in order to increase the reaction between the first layer 110 and the activating material AM, the user may press the film 100 using, for example, a puff on the first layer 110 on which the activating material AM is applied. Under pressure, the activating material AM may penetrate into the interior of the first layer 110.

Figure 8:
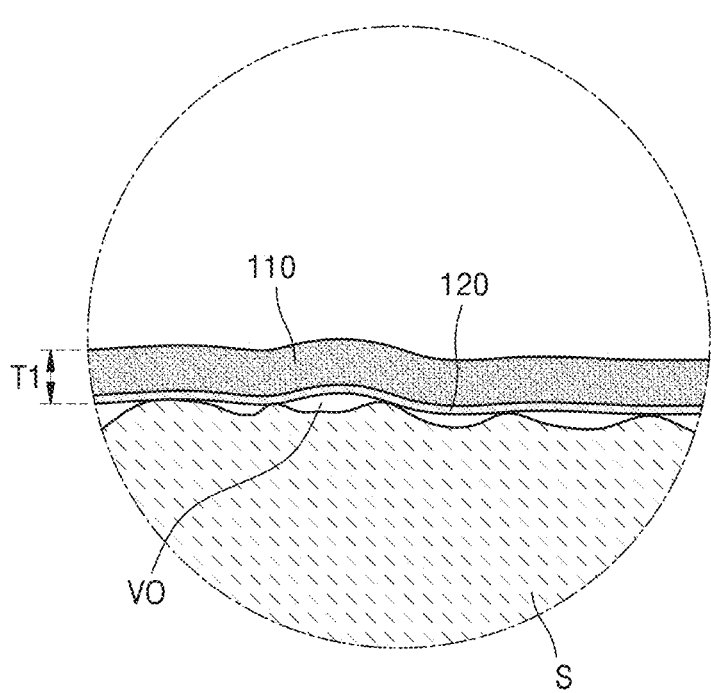

Referring to FIG. 8, when the skin attachment patch 1 is attached on the skin S, a void VO may be formed between the film 100 and the skin S by an uneven surface of the skin S. The void VO formed between the film 100 and the skin S may reflect or distort visible light coming from the outside.

Thus, when viewed from the outside, the film does not look transparent, and wrinkles may be easily formed.

Referring to FIG. 9, when the film 100 is activated by the activating material AM, the thickness of the first layer 110 may be decreased from the first thickness T1 to the first' thickness T1' so that the film 100 becomes softer and is more adhesive to the skin. That is, the first layer 110 may be attached to fit the uneven surface of the skin S, so that the void VO may be removed. In an embodiment, the thickness of the first layer 110 may be decreased and the transparency thereof may be increased.

Figure 12:
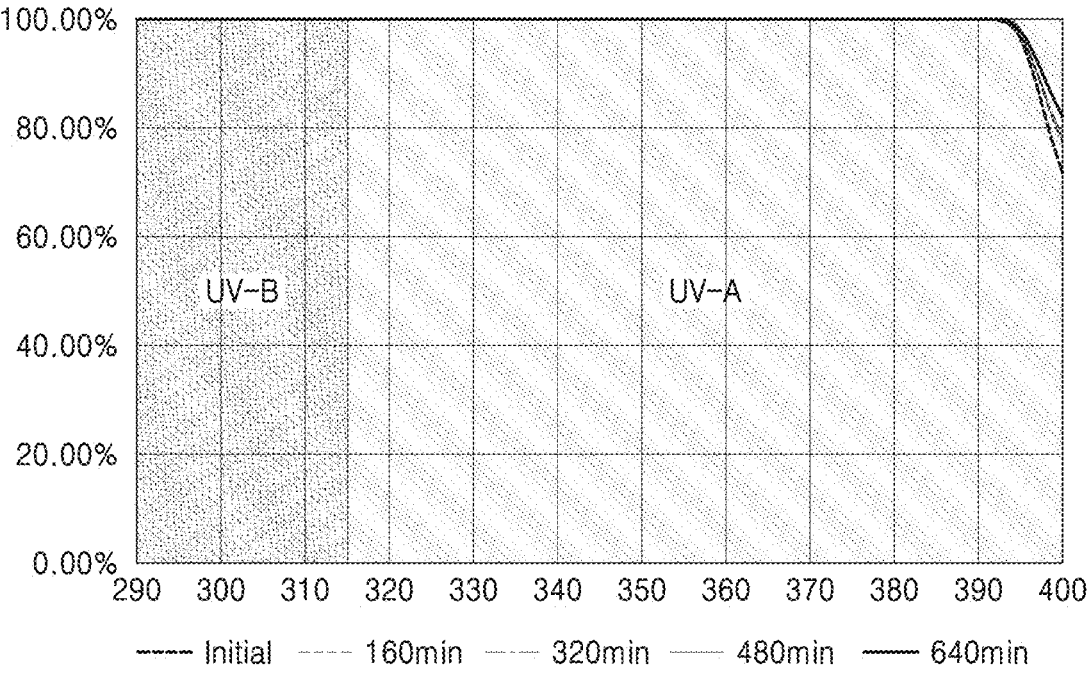
FIGS. 12 and 13 are graphs illustrating the ultraviolet (UV) blocking effect of the skin attachment patch illustrated in FIG. 1.
Figure 13:
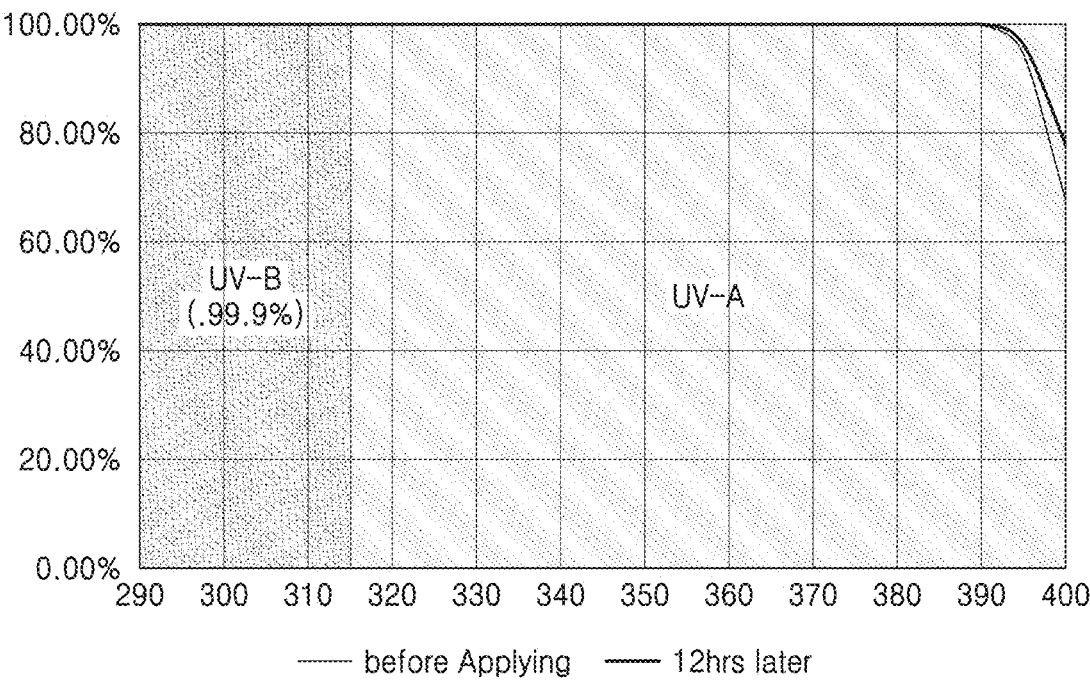

FIGS. 12 and 13 are graphs illustrating the UV blocking effect of the patch for attachment on the skin illustrated in FIG. 1.

The skin attachment patch of FIGS. 12 and 13 includes a UV blocking material in a film, and may have UV blocking performance, water resistance (FIG. 12) and blocking retention (FIG. 13). In the graphs, the x-axis represents the wavelength, and the y-axis is defined as the blocking rate.

When the thickness of the skin attachment film was 25 nm, the UV protection factor (UPF) of the film was 343, the UV-B blocking ratio was 99.9% and the UV-A blocking ratio was 95.8%.

When the thickness of the skin attachment film was 35 nm, the UV protection factor (UPF) of the film was 343, the UV-B blocking ratio was 99.9% and the UV-A blocking ratio was 97.4%.

In the water resistance test, the skin attachment patch was fixed on a 96 well plate, and an experimental environment was provided such that both the inner and outer surfaces of the skin attachment film was immersed in water. Immersing (20 min) and drying (20 min) were repeatedly performed.

In the graph of FIG. 12, 160 min refers to a case where immersing and drying were performed 8 times, 320 min refers to a case where immersing and drying were performed 16 times, 480 min refers to a case where immersing and drying were performed 24 times, and 640 min refers to a case where immersing and drying were performed 32 times. Even when the patch for attachment on the skin was repeatedly immersed and dried, the UV protection efficiency was not decreased. In particular, it was confirmed that even if the patch for attachment on the skin was repeatedly immersed and dried, almost 100% blocking efficiency was maintained in the UV-B wavelength band, and the UV-A wavelength band of 390 nm or lower.

In an embodiment, even when physical stimulation with ultrasound is applied to the skin attachment patch, the UV blocking efficiency is not decreased.

In the blocking retention test, a skin attachment patch was attached on the skin, and the UV blocking effect was measured at the initial time point and after 12 hours. Even after 12 hours have elapsed since the skin attachment patch is attached on the skin, the UV protection efficiency is not decreased.

UV protection products that are applied to the skin need to be applied continuously at 2 hour intervals to maintain UV protection performance. This is because, even when a cream-type sunscreen product is applied, the blocking rate is decreased due to sweat, physical contact, a decrease in the effectiveness of the sunscreen, and the absorption of sunscreen into the skin.

In the case of the patch for attachment on the skin of the present disclosure, even when the patch is attached on the skin and the film is activated, water resistance is maintained and blocking power is maintained. Unlike cream-type sunscreens of the prior art, in the case of the skin attachment patch of the present disclosure, UV protection efficiency may not be decreased by external environments such as water after being attached once, and UV rays may be continuously blocked.

Table 1 shows an experimental result confirming whether the following test items were detected after exposing the skin attachment patch of the present disclosure to water or an activating material for 24 hours.

The skin attachment patch according to the present disclosure may be selected from ingredients having UV absorption/blocking functions. In this test, a plurality of skin attachment patches including at least one of the ingredients in Table 1 were used, and in each test, the following ingredients were not detected even when exposed to water or an activating material for a long time.

TABLE 1

| Test Items | Unit | Results | R.L | Remarks |
|---|---|---|---|---|
| Ethylhexyl-methoxycinnamate | µg/g | non-detection | 10 | In House Method (HPLC-UVD) |
| Butylmethoxy-dibenzoylmethane | µg/g | non-detection | 10 | |
| homosalate | µg/g | non-detection | 10 | |
| Ethylhexylsalicylate | µg/g | non-detection | 10 | |
| Phenylbenzimidazole sulfonic acid | µg/g | non-detection | 10 | |
| Octocrylene | µg/g | non-detection | 10 | |
| Benzophenone-4 | µg/g | non-detection | 10 | |
| Benzophenone-8 | µg/g | non-detection | 10 | |

When the skin attachment patch of the present disclosure is exposed to water or activating material for a long time, a corresponding component is not detected. It is confirmed that the component is contained inside the film and does not leak to the outside. In particular, even when the film is exposed to the activating material, the activating material only melts the base material, and the component contained therein does not leak to the outside.

The skin attachment patch according to the present disclosure may cause less skin troubles because the ingredients thereof do not leak even when exposed to the external environment. In particular, even when the skin attachment patch is activated, only the base material is melted and the thickness of the film is decreased, and the ingredients contained inside do not leak, so that stability may be secured.

FIG. 14 shows an image of the skin attachment patch of FIG. 1 during use on the skin.

(A) of FIG. 14 shows an image of the skin after the skin attachment patch is attached on the skin and before the film is activated. As shown in (A), since the portion on which the film is attached is in a glossy state, the glossy area on which the film is attached is easily distinguished from the matt area on which the film is not attached.

(B) of FIG. 14 is divided into an upper portion and a lower portion, wherein the upper portion is an area in which the film is not activated, and the lower portion is an area in which the film is activated. The upper portion of (B) is maintained in a glossy state, but the lower portion thereof is hanged to a matte state by activation. The upper glossy area and the lower matte area may be easily distinguished from each other.

A skin attachment patch and a method of using the same according to an embodiment of the present disclosure may provide improved adhesion in a part where the patch is to be attached, thereby improving the feeling of use. The patch for attachment on the skin may have a decreased film thickness and improved softness. A softer film may improve adhesion by removing the void between the surface of the skin and the film.

A skin attachment patch and a method of using the same according to an embodiment of the present disclosure may provide improved transparency to a portion of the film which is attached, resulting in improved cosmetic effect, and enhanced comfort during attachment. The skin attachment patch includes a film of which thickness is decreased and transparency is enhanced. The skin can be clearly exposed through the transparent portion, which may increase user's satisfaction.

The skin attachment patch and the method of using the same according to an embodiment of the present disclosure may have improved functionality. The part thereof in contact with the skin contains effective materials that are delivered to the skin, so that skin troubles may not occur and the cosmetic effect may be enhanced. A film containing a UV blocking material may have high waterproof performance, high waterproof retention performance, and high UV blocking performance.

As such, the present disclosure has been described with reference to the embodiments shown in the drawings, but the embodiments are only an example, and those of ordinary skill in the art would understand that various modifications and equivalent other embodiments are possible therefrom. Therefore, the technical protection scope of the present disclosure should be determined by the technical idea of the appended claims.

What is claimed is:

1. A patch for attachment on the skin, comprising:
a base sheet; and
a film disposed on the base sheet,
wherein the film includes:
a first layer adjacent to the base sheet, the first layer configured such that, in response to application of an activating material to the film, at least a portion of the first layer is melted, thereby decreasing a thickness of the first layer, and
a second layer arranged on one side of the first layer and including an effective material configured to be delivered to the skin,
wherein a transparency of the film increases as the thickness of the first layer decreases.

2. The patch of claim 1, wherein the activating material is configured to be sprayed on the film.

3. The patch of claim 1, wherein in response to application of the activating material to the film, the film becomes softer.

4. The patch of claim 1, further comprising:
an interlayer arranged between the first layer and the base sheet, wherein the interlayer has a smaller adhesive force than the second layer.

5. The patch of claim 4, wherein the interlayer is configured such that, in response to contact with a solution, an adhesive force of the interlayer is decreased.

6. A method of using the patch of claim 1 for attachment to skin, the method comprising:
attaching the film to the skin; and
applying an activating material to the film to decrease a thickness of the film.

* * * * *